United States Patent [19]

Griffith et al.

[11] Patent Number: 4,911,924

[45] Date of Patent: Mar. 27, 1990

[54] INDUCTION OF ANTIBIOTIC HYPERSENSITIVITY IN TETRACYCLINE-RESISTANCE MICROORGANISMS

[75] Inventors: Jeffrey K. Griffith, Cedar Crest; William L. Anderson, Albuquerque, both of N. Mex.

[73] Assignee: University of New Mexico, Albuquerque, N. Mex.

[21] Appl. No.: 39,171

[22] Filed: Apr. 17, 1987

[51] Int. Cl.$^4$ .................. A61K 35/00; A61K 35/74
[52] U.S. Cl. .................................... 424/114; 514/152; 514/154
[58] Field of Search ................ 514/152, 154; 424/114

[56] References Cited

U.S. PATENT DOCUMENTS

| | | | |
|---|---|---|---|
| 2,777,791 | 1/1957 | Visor et al. | 424/114 |
| 2,801,950 | 8/1957 | Tate | 424/114 |
| 2,813,820 | 11/1957 | English et al. | 424/114 |
| 2,866,708 | 12/1958 | Broquist et al. | 424/114 |
| 3,061,513 | 10/1962 | English et al. | 424/114 |
| 3,087,858 | 4/1963 | Buckwalter et al. | 424/114 |
| 3,156,617 | 11/1964 | Granatek et al. | 424/114 |
| 3,375,165 | 3/1968 | Hagermann et al. | 424/114 |
| 3,642,987 | 2/1972 | Bergy et al. | 424/114 |
| 3,725,543 | 4/1973 | Konopka et al. | 424/114 |
| 4,399,127 | 8/1983 | Hacke et al. | 424/227 |
| 4,452,778 | 6/1984 | Brier | 424/114 |
| 4,501,732 | 2/1985 | Kulesár et al. | 424/114 |
| 4,552,763 | 11/1985 | Brier | 424/114 |

*Primary Examiner*—John Kight
*Assistant Examiner*—Nathan M. Nutter
*Attorney, Agent, or Firm*—Jean A. Buttmi; Charles W. Fallow

[57] ABSTRACT

Microorganisms carrying tetracycline-resistant determinants are hypersensitized to Sm- and 2-DOS- aminoglycoside antibiotics by exposure to subinhibitory amounts of tetracycline inducer.

54 Claims, No Drawings

INDUCTION OF ANTIBIOTIC HYPERSENSITIVITY IN TETRACYCLINE-RESISTANCE MICROORGANISMS

BACKGROUND OF THE INVENTION

1. Field of the Invention

Drug-resistant microorganisms pose a serious threat to effective clinical management of infectious diseases. It is well-settled that microorganism drug-resistance is afforded by both extrachromosomal resistance determinants and random mutation of the cells; in the presence of the drug, these provide a selection advantage for the survival of the resistant bacteria. While mechanisms of drug-resistance vary, and in many instances are poorly understood, it is believed that for many drugs, including tetracycline, resistance is a function of cellular membrane efflux of the drug controlled by genetic information encoded in extrachromosomal plasmids. The resistance trait can be transmitted from resistant to sensitive organisms by transferal of the genetic material itself via resistance transfer factors carried by the cell. It is this genetically-mediated transfer of bacterial drug resistance traits which presents the most serious clinical implications, particularly when multiple-drug resistance is involved.

2. Discussion of Related Art

The clinical treatment of infectious diseases has thus been often designed to obviate the development of a drug-resistant microorganism population insofar as possible. In particular, combinations of antibiotics are often favored in antibiotic therapy to suppress the emergence of mutants expressing resistance to an individual drug employed in the therapy, particularly in the treatment of infectious diseases caused by microorganisms which tend rapidly to mutate to resistant strains. While synergistic effects have been reported for some of these combinations, the thrust of this therapy has been to treat the infection with minimum inhibitory concentrations (MIC) of one or more antibiotics to inhibit the growth of the infecting bacteria, including singly drug-resistant mutant strains, and increase the spectrum of sensitive microorganisms targeted by the drugs. While this approach is relatively successful in combating drug-resistant populations arising from random mutations, it is of little effect in the treatment of microorganisms with constitutive resistance (i.e., those carrying extrachromosomal resistance determinants) to one or more therapeutic drugs of first choice Accordingly, the infecting resistant microorganisms are treated with drugs which are of less clinical value, usually owing to their association with adverse side effects at effective dosage levels. In particular, diseases caused by microorganisms containing tetracycline resistance determinants are commonly managed by treatment of the host with a drug of lesser choice, frequently an aminoglycoside antibiotic; at the antibiotic dosages typically employed, however, aminoglycoside and nephro- toxicity are serious and not uncommon clinical problems. It is thus desirable to improve such alternative therapy to decrease risk of toxicity while maintaining or improving efficacy.

SUMMARY OF THE INVENTION

The invention is directed to a method for hypersensitizing microorganisms which contain tetracycline-resistance determinants (Tc$^r$) to the action of an aminoglycoside antibiotic, comprising exposing the Tc$^r$ microorganism to a subinhibitory amount of one of a class of tetracycline-related compounds to induce expression of the tetracycline-resistance determinant and sensitize the microorganism to antibiotic therapy. Hypersensitization according to the invention permits the clinical use of much lower minimum inhibitory concentrations of aminoglycoside antibiotic than would otherwise be required, with concomitant reduced risk of drug toxicity. Further, the resulting increased potency of the antibiotics against Tc$^r$ strains is also exploitable to achieve a more rapid effect, or to treat marginally susceptible bacteria at conventional dosage levels. Effects comparable to those obtained with conventional aminoglycoside therapy are thus obtainable at lower dosage levels, or, conversely, the antibiotic is more effective at conventional dosage levels.

DETAILED DESCRIPTION OF THE INVENTION

It has been postulated that microorganisms expressing tetracycline resistance are characterized by a component of the cytoplasmic membrane styled TET-protein, which mediates movement of tetracycline across the membrane and out of the cell. In addition to mediating the efflux of tetracycline from the cell membrane, the presence of TET-protein appears to be associated with microorganism hypersensitivity to a variety of compounds, especially lipophilic chelators such as fusaric acid (see, e.g., *J. Bact.* 143:926–933, 1980).

It has now been discovered that a subinhibitory amount of tetracycline or a tetracycline-related compound is effective to hypersensitize tetracycline resistant microorganisms to the action of aminoglycosideantibiotics containing streptamine or 2-deoxystreptamine functional groups. It is believed that tetracycline functions to induce the expression of TET-resistance in the microorganism, probably by the production of TET-protein, which then promotes the uptake of the therapeutic antibiotic by the cell. Therapeutic regimens employing reduced minimum inhibitory concentrations (MICs) of aminoglycoside antibiotics against tetracycline resistant bacteria are accordingly practical.

The microorganisms hypersensitizable according to the invention are those genetically resistant to tetracycline, i.e., microorganisms carrying extrachromosomal tetracycline resistance determinants. Clinically, the infecting strain of Tc$^r$ microorganism is characteristically a strain of bacteria, especially Gram-negative bacteria. While microorganisms vary in their responses to a drug, an art-accepted definition of a tetracycline resistant microorganism is a microorganism for which the minimum inhibitory concentration of tetracycline is greater than about 12.5 ug/ml, especially greater than about 16 ug/ml Physicians' Desk Reference: 38th edition, Med. Econ. Co., Orodell, New Jersey—pub. (1984) pgs. 1058, 1527, 1941]. Typically, resistant strains according to the invention are those wherein the MIC is greater than about 50 ug/ml.

The inducers are clinically employed against Tc$^r$ microorganisms in amounts sufficient to provide the desired hypersensitivity to the therapeutic antibiotic. While, as previously noted, this hypersensitivity is associated with induction of TET-protein production, hypersensitivity may also be associated with induction of abnormal or modified TET-proteins which do not themselves function to mediate TET-resistance in Tc$^r$ microorganisms, but which do function to mediate hypersensitivity to the aminoglycoside antibiotic. The increase in aminoglycoside sensitivity will vary according to several factors, including the class of Tc$^r$ determinant present, the type of plasmid on which the determinant is located, and the particular microorganism expressing the TET gene. The correlation between in vivo and in vitro results is high, however, and optimum dosages for clinical use can be readily determined by preliminary treatment of the pathogen with inducer and antibiotic in vitro, as illustrated by the Examples set forth herein. In the practice of the invention, the inducer is further employed in an amount providing a subinhibitory concentration (clinically, a subinhibitory serum concentration) for the infecting resistant microorganism. For microorganisms characterized by a resistance to tetracycline serum concentrations of more than about 50 ug/ml, subinhibitory serum concentrations of less than about 50 ug/ml of antimicrobially active inducer are employable. Similarly, lower subinhibitory concentrations are employable according to the lower resistance characteristics of the infecting microorganism.

The tetracycline employed is selected from a class of tetracycline-related compounds herein referred to as "inducers", defined as compounds containing a tetracycline nucleus which do not necessarily themselves exhibit antibiotic properties, but which are capable of inducing Tc$^r$ expression, or the production of TET-protein, in the Tc$^r$ microorganism. The class includes compounds characterized by a tetracycline nucleus (I) which is unsubstituted or substituted with one or more groups $R_1$-$R_{11}$, which are selected with the proviso that the resulting compound functions to induce Tc$^r$ expression as described, and is non-toxic in clinical use.

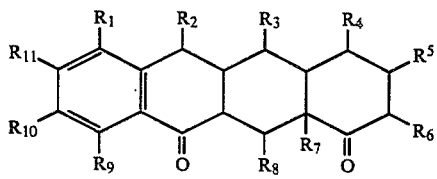

Microbially active compounds of the formula (I) include those compounds wherein $R_5$, $R_7$, $R_8$ and $R_9$ are OH; $R_4$ is N(CH$_3$)$_2$; and $R_6$ is CONH$_2$; and especially such compounds wherein:
$R_1$ is H, Cl, or N(CH$_3$)$_2$;
$R_2$ is CH$_3$OH, OH, CH$_2$, CH$_3$, or H;
$R_3$ is H or OH; and
$R_{10}$ and $R_{11}$ are H.

The class further includes non-microbially active compounds of the formula I, such as those wherein $R_1$-$R_5$ and $R_7$-$R_{11}$ are as defined above and $R_6$ is COOH, many of which are excellent inducers. Compounds suitable for use in the process of the invention are further described in the literature, especially *Antimicrobial Drug Resistance,* "Resistance to the Tetracyclines" Academic Press, Inc. (1984), pp. 191–240, incorporated herein by reference. Compounds of the formula (I) which are biologically modified, such as acid-inactivated tetracycline, are also useful in the practice of the present invention. Inducers comprising tetracycline, chlortetracycline, oxytetracycline, demeclocycline, methacycline, doxycycline and minocycline are particularly contemplated.

As previously noted, microorganisms treatable according to the present invention typically have a tetracycline resistance of at least about 12.5 ug/ml, and usually at least about 16 ug/ml, and for these organisms, concentrations of active inducers of below about 12.5 or 16 ug/ml, respectively, are thus subinhibitory. Generally, for most resistant microorganism strains within the scope of the invention, serum concentrations substantially below the minimum inhibitory concentration are employed. Subinhibitory inducer serum concentrations of less than about 4 ug/ml, typically, less than about 2 ug/ml, and more typically, less than about 1 ug/ml, are ordinarily sufficient to hypersensitize Tc$^r$ strains infecting mammals, especially humans, to the selected aminoglycoside antibiotic, and are preferred in practice. Since serum levels high enough to inhibit resistant strains are not clinically attempted in vivo, tetracycline or related active compounds are not presently employed alone or in combination with other drugs to treat clinically pathogens which are consecutively tetracycline-resistant, especially highly resistant strains of the type having a resistance of greater than about 50 ug/ml. In applications wherein non-microbially active inducers are employed (i.e., those which would not inhibit growth of the tetracycline-resistant microorganism in any clinically contemplated amount), the term "subinhibitory" is defined as a non-toxic amount sufficient to hypersensitize the microorganism. Typically, the amounts employed are comparable to the subinhibitory amounts of the microbially-active inducers employed.

The expression of the TET gene induced by treatment of the resistant pathogen with the tetracycline or tetracycline related inducer according to the invention mediates the potency of aminoglycoside antibiotics which contain either streptamine or 2-deoxystreptamine in the structure thereof:

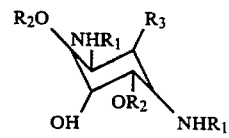

wherein:
$R_1$ is —H, —CH$_3$, —CH$_2$CH$_3$, or guanido group
$R_2$ is —H, or glycosidic bond
$R_3$ is —H or —OH Exemplary therapeutic antibiotics within this class include kanamycin, amikacin, gentamicin, tobramycin, netilmicin, sisomicin, streptomycin, neomycin, paromomycin, and apramycin. Kanamycin, amikacin, gentamicin, tobramycin and streptomycin appear to be of particular clinical and veterinary interest at the present time. Since hypersensitization according to the invention appears to render the Tc$^r$ cells consistently vulnerable to compounds containing streptamine (Sm) or 2-deoxystreptamine (2-DOS) moieties, it is contemplated that clinical treatment of Tc$^r$ pathogens with subinhibitory amounts of inducer according to the invention will hypersensitize these pathogens to a variety of compounds containing these streptamine or 2-deoxystreptamine moieties. It is particularly contemplated that the efficacy of natural antibiotics and other drugs such as chloramphenicol, rifampicin, or ampicillin, which do not contain 2-DOS- or Sm- moieties, and to which Tc$^r$ microorganisms are not hypersensitizable according to the process of the invention, can be significantly improved by the expedient of attaching Sm- or 2-DOS moieties to the nuclei thereof in conventional manner, followed by hypersensitization with a tetracycline inducer according to the invention Derivitization of synthetic antibiotics and other drugs to provide one or more Sm- or 2-DOS- functional groups on the molecule for use in therapeutic treatment according to the invention is also possible, provided that the derivatives are not toxic to the host in the required therapeutic amounts. Modification of compounds which are too toxic for use per se with 2-DOS or Sm moieties for clinical use at decreased dosage levels is also within the scope of the invention. The antibiotics are administered as well-understood in the art, in therapeutic amounts sufficient to inhibit growth of the infecting mircroorganism. While the inducer and antibiotic may be administered together, sequential administration over a period of time sufficient to first permit inducement of $Tc^r$ expression is often preferable.

The Examples which follow demonstrate that bacteria carrying tetracycline-resistant determinants are more susceptible to Sm- or 2-DOS- glycosides after induction with an inducer according to the invention, and that the in vitro results correlate with in vivo studies. It is noted that throughout the disclosure, including the following Examples, the expression "ug" means "micrograms".

EXAMPLES

METHODOLOGY:

The antibiotic concentration that reduces bacterial plating efficiency by 90% (the $LD_{90}$) in vitro was determined as follows: Aliquots of exponentially growing cultures of the specified bacteria containing $2-5\times10^3$ cells were spread on L-agar plates containing a range of concentrations of the indicated antibiotics and after incubation at 37° C. for 24–36 hours the number of colonies was determined.

The antibiotic concentration that reduced bacterial survival by 90% in vivo was determined as follows: Virulent $Tc^s$ (tetracycline-sensitive) and $Tc^r$ K−1 $E.$ $coli$ strains were grown on blood agar plates at 37° C. The bacteria were scraped from the plates and washed by centrifugation through buffered saline. Aliquots containing $3\times10^6$ cells in one ml. of buffered saline were injected into the peritoneal cavities of groups of 3–5 male mice, using one group for each antibiotic concentration to be tested. Two hours later, the specified amounts of antibiotic in one ml. of buffered saline were injected into the peritoneal cavities. Seven hours after the injection of the bacteria, the animals were killed, the contents of the peritoneal cavities removed, and the number of surviving bacteria determined by plating on L-agar.

EXAMPLES

EXAMPLES 1–5

The $LD_{90}$s on kanamycin of $E.$ $coli$ K−12 strain HB101 containing the inducible tet genes carried by plasmids pSC101, pCC42, (class C tet genes), plasmid pJOE105 (class A tet gene), transposon Tn10 (class B tet gene) and plasmid pSL101 (class D tet gene) were compared with and without induction of the tet genes by exposure to either 0.5–1.0 ug/ml of medium Tc or acid-inactivated Tc (ATC), an inducer that lacks antimicrobial activity. These strains are resistant to Tc serum concentrations of from about 40–250 ug/ml, depending on which tet gene they contain. Thus, the inducing concentration of Tc is far below that needed for antibacterial activity. The strains induced with Tc (or ATC) had $LD_{90}$ values that were approximately 25%, 50%, 25%, 40%, and 15% lower, respectively, than paired controls that had not been induced with Tc or ATC (Both inducers have been used interchangeably with comparable results).

EXAMPLES 6–9

The $LD_{90}$ on kanamycin of $Tc^r$ clinical isolates of $E.$ $coli$, Proteus and Klebsiella was compared with and without induction with Tc at 1 ug/ml. Each of these strains was resistant to at least 20 ug/ml Tc. Therefore the inducing Tc concentration is far below that which would have antibacterial activity against these strains. The $LD_{90}$ of the $E.$ $coli$ strain, two Proteus strains and the Klebsiella strain which had been induced with 1 ug/m/ tc were approximately 20%, 25%, 25% and 20% lower than the $LD_{90}$ of the same strains which had not been induced. Similarly, the $LD_{90}$ on amikacin of 22 isolates of $E.$ $coli$ were compared with and without induction with Tc at 1 ug/ml. Thirteen out of twenty-two $LD_{90}$s of the induced strains were lower than the $LD_{90}$s of the non-induced strains.

EXAMPLE 10

The $LD_{90}$ on amikacin of a $Tc^r$ clinical isolate of $E.$ $coli$ which was also resistant to kanamycin was compared on amikacin with and without induction with 1 ug/ml Tc. The $LD_{90}$ of the induced sample was approximately 35% lower than the $LD_{90}$ of the paired control which had not been induced with Tc.

EXAMPLE 11

The $LD_{90}$ on kanamycin of the virulent $Tc^r$ K−1 $E.$ $coli$ strain LA396 containing plasmid pBR322 was compared to the $LD_{90}$ of the plasmid-free $Tc^s$ control in vivo. The $LD_{90}$ of the $Tc^r$ strain was approximately 50% lower than the $LD_{90}$ of the $Tc^s$ control at a dosage level of 75 ug antibiotic per animal.

Examples 1–5 demonstrate that increased susceptibility of $Tc^r$ bacteria to aminoglycoside antibiotics is induced when cells containing a representative of each of the four classes of Tc resistance genes which have been described in Gram-negative bacteria are exposed to subinhibitory concentrations of a tetracycline inducer. Examples 6–10 demonstrate that increased susceptibility is similarly induced when clinically isolated pathogens are exposed to subinhibitory concentrations of tetracycline. Example 11 demonstrates that the increased susceptibility is expressed in vivo in a mouse model of peritonitis. It is thus apparent that the process according to the present invention increases aminoglycoside efficacy, with reduced risk of toxicity.

What is claimed is:

1. A method for hypersensitizing a microorganism carrying a tetracycline-resistant determinant to a therapeutic antibiotic containing at least one streptamine or 2-deoxystreptamine functional group, comprising first exposing the microorganism to a subinhibitory concentration of a tetracycline inducer in an amount and for a period of time sufficient to induce expression of tetracycline resistance and to hypersensitize the microorganism to the therapeutic antibiotic and thereafter exposing the microorganism to the therapeutic antibiotic.

2. The method of claim 1, wherein the microorganism is a bacteria.

3. The method of claim 2, wherein the microorganism is a Gram-negative bacteria.

4. The method of claim 1, wherein the microorganism is resistant to a tetracycline serum concentration of at least about 12.5 ug/ml.

5. The method of claim 4, wherein the microorganism is resistant to a tetracycline serum concentration of at least about 16 ug/ml.

6. The method of claim 5, wherein the microorganism is resistant to a tetracycline serum concentration of at least about 50 ug/ml.

7. The method of claim 1, wherein the subinhibitory concentration is less than about one-half the minimum inhibitory serum concentration.

8. The method of claim 4, wherein the subinhibitory concentration of tetracycline inducer employed is less than about 4 ug/ml.

9. The method of claim 8, wherein the subinhibitory concentration is less than about 2 ug/ml.

10. The method of claim 9, wherein the subinhibitory concentration is less than about 1 ug/ml.

11. The method of claim 1, wherein the therapeutic antibiotic is an aminoglycoside antibiotic.

12. The method of claim 1, wherein the therapeutic antibiotic is kanamycin, amikacin, gentamicin, tobramicin, or streptamicin.

13. The method of claim 12, wherein the therapeutic antibiotic is kanamycin.

14. The method of claim 1, wherein the tetracycline inducer is antimicrobially-active.

15. The method of claim 1, wherein the tetracycline inducer is tetracycline, chlortetracycline, xytetracycline, demeclocycline, methacycline, doxycycline, or minocycline.

16. The method of claim 1, wherein the tetracycline inducer is antimicrobially inactive.

17. The method of claim 1, wherein the tetracycline inducer is tetracycline or acid-inactivated tetracycline.

18. The method of claim 1, wherein the tetracycline inducer contains a tetracycline nucleus and is substantially non-toxic at the dosage levels employed.

19. The method of claim 2, wherein the inducer is tetracycline.

20. A method for treating a mammal infected with a tetracycline-resistant microorganism comprising:
(a) first administering to the mammal an amount of tetracycline inducer sufficient to obtain a serum concentration of tetracycline inducer subinhibitory to the infecting microorganism and also sufficient to hypersensitize the microorganism to a therapeutic antibiotic containing at least one streptamine or 2-deoxystreptamine functional group; and
(b) thereafter administering an amount of the therapeutic antibiotic sufficient to provide a serum concentration thereof which is at least a minimum inhibitory serum concentration for the hypersensitized microorganism.

21. The method of claim 20, wherein the microorganism is resistant to a subinhibitory serum concentration of tetracycline inducer of at least about 50ug/ml, and the serum concentration of inducer is less than about 50ug/ml.

22. The method of claim 20, wherein the therapeutic antibiotic is gentamicin.

23. The method of claim 20, wherein the mammal is a human.

24. The method of claim 20, wherein the microorganism is a bacteria.

25. The method of claim 24, wherein the microorganism is a Gram-negative bacteria.

26. The method of claim 20, wherein the microorganism is resistant to a tetracycline serum concentration of at least about 12.5 ug/ml.

27. The method of claim 26, wherein the microorganism is resistant to a tetracycline serum concentration of at least about 16 ug/ml.

28. The method of claim 27, wherein the microorganism is resistant to a tetracycline serum concentration of at least about 50 ug/ml.

29. The method of claim 20, wherein the subinhibitory serum concentration of tetracycline inducer obtained is less than about one-half the minimum inhibitory serum concentration for the microorganism.

30. The method of claim 20, wherein the subinhibitory concentration is less than about 4 ug/ml.

31. The method of claim 30, wherein the subinhibitory concentration is less than about 2 ug/ml.

32. The method of claim 3!, wherein the subinhibitory concentration is less than about 1 ug/ml.

33. The method of claim 20, wherein the therapeutic antibiotic is an aminoglycoside antibiotic.

34. The method of claim 33, wherein the antibiotic is kanamycin, amikacin, gentamicin, tobramicin, or streptomicin.

35. The method of claim 34, wherein the antibiotic is kanamycin.

36. The method of claim 20, wherein the inducer is antimicrobially-active.

37. The method of claim 20, wherein the tetracycline inducer is tetracycline, chlortetracycline, oxytetracycline, demeclocycline, methacycline, doxycycline, or minocycline.

38. The method of claim 20, wherein the tetracycline inducer is antimicrobially inactive.

39. The method of claim 20, wherein the tetracycline inducer is tetracycline or acid-inactivated tetracycline.

40. The method of claim 20, wherein the tetracycline inducer contains a tetracycline nucleus and is substantially non-toxic at the dosage levels employed.

41. The method of claim 24, wherein the tetracycline inducer is tetracycline.

42. The method of claim 23, wherein the microorganism is a Gram-negative bacteria resistant to a tetracycline serum concentration of at least about 50 ug/ml and the tetracycline inducer is administered in an amount sufficient to provide a subinhibitory serum concentration of inducer of less than about half the minimum inhibitory concentration.

43. The method of claim 42, wherein tetracycline inducer is tetracycline, chlortetracycline, oxytetracycline, demeclocyline, methacycline, doxycycline, or minocycline.

44. The method of claim 42, wherein the therapeutic antibiotic is an aminoglycoside antibiotic.

45. The method of claim 23, wherein the therapeutic is an aminoglycoside antibiotic.

46. The method of claim 42, wherein the therapeutic antibiotic is kanamycin, amikacin, gentamicin, tobramicin, or streptamicin.

47. The method of claim 43, wherein the therapeutic antibiotic is kanamycin, amikacin, gentamicin, tobramicin, or atreptamicin.

48. The method of claim 46, wherein the therapeutic antibiotic is kanamycin.

49. The method of claim 20, wherein the therapeutic antibiotic is kanamycin.

50. The method of claim 49, wherein the tetracycline inducer is tetracycline or acid-inactivated tetracycline.

51. The method of claim 1, wherein the therapeutic antibiotic is gentamicin.

52. The method of claim 46, wherein the therapeutic antibiotic is gentamicin.

53. The method of claim 51, wherein the tetracycline inducer is tetracycline.

54. The method of claim 52, wherein the tetracycline inducer is tetracycline.

* * * * *